Figure 1:
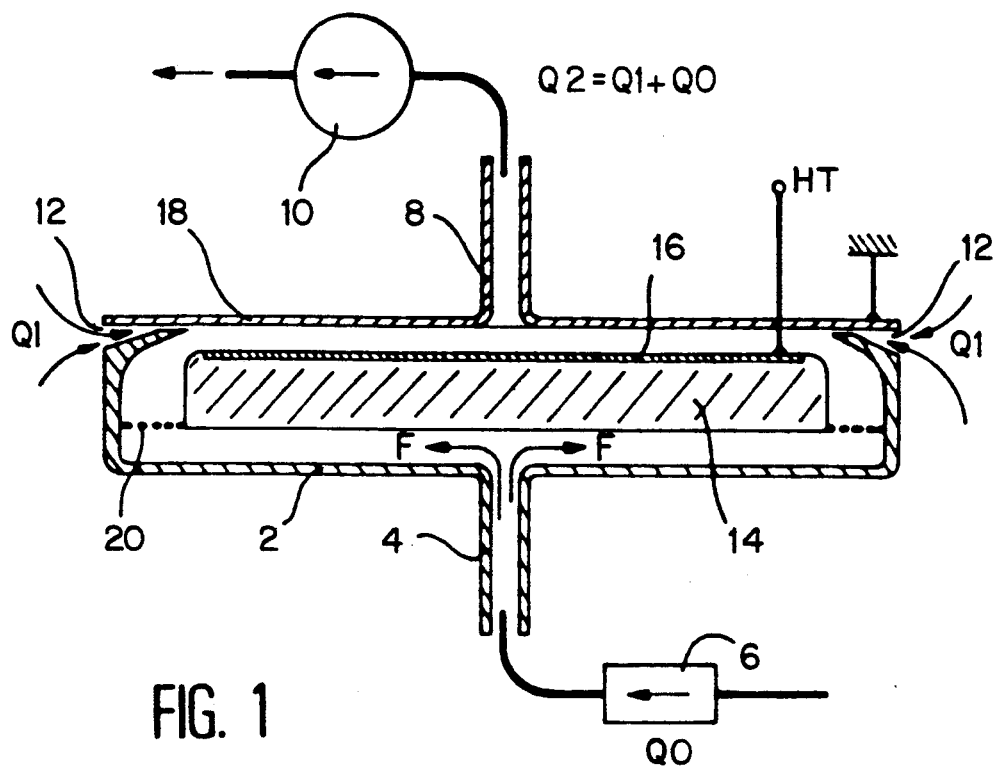

United States Patent [19]

Pourprix

[11] Patent Number: 5,150,036
[45] Date of Patent: Sep. 22, 1992

[54] PROCESS AND APPARATUS FOR CALIBRATING A PARTICLE COUNTER

[75] Inventor: Michel Pourprix, Montlhery, France

[73] Assignee: Commissariat a l'Energie Atomique, Paris, France

[21] Appl. No.: 661,824

[22] Filed: Feb. 26, 1991

[30] Foreign Application Priority Data

Feb. 27, 1990 [FR] France .................. 90 02414

[51] Int. Cl.⁵ .................. G01N 15/02; G06M 11/00
[52] U.S. Cl. .................. 324/71.4; 377/10; 377/29; 73/1 G; 73/28.02; 324/601
[58] Field of Search .................. 377/10, 11, 29; 324/71.4, 71.1, 464, 601; 73/1 G, 28.02

[56] References Cited

U.S. PATENT DOCUMENTS

| | | | |
|---|---|---|---|
| 3,413,545 | 11/1968 | Whitby | 324/71.1 |
| 4,331,862 | 5/1982 | Ryan | 377/29 |
| 4,556,849 | 12/1985 | Kalakutsky et al. | 324/464 |
| 4,854,153 | 8/1989 | Miyagawa et al. | 73/1 G |

OTHER PUBLICATIONS

"Equilibrium bipolar charge distribution of aerosols" by B. Y. Lui et al., in: Journal of Colloid and Interface Science, vol. 49, No. 2, Nov. 1974, pp. 305-312, (Liv et al.).

"Electrical aerosol analyzer: calibration and performance" by D. Y. Pui et al., in: Aerosol Measurement, D. Lundgren, 1979, pp. 384-399 (Pui et al.).

"Erzeuging von Prueaerosolen fuer die Kalibrierung von optishen Partikelmessverfahren nach VDI 3491" by C. Helsper et al., in: TM Technisches Messen, vol. 56, No. 5, May 1989, pp. 229-234, (Helsper et al).

Primary Examiner—John S. Heyman
Attorney, Agent, or Firm—Michael N. Meller

[57] ABSTRACT

A process and apparatus for calibrating a particle counter is described. The process comprises the steps of forming a vector gas flow by an aerosol of particles of the same grain size, developing ions in the vector gas with both sign by a bipolar charger, certain particles being electrically charged to a stationary charge state in which the distribution of the number of charges fixed to each particle follows a Gaussian law (Gunn or Boltzmann), passing the charge aerosol into a mobility selector to attract the charged particles to electrodes therein and classify them as a function of the numbers p of their elementary electrical charges e and allowing the electically neutral particles to escape, collecting the neutral particles and passing the neutral particles into the particle counter to be calibrated, the particles counter displaying a value $N'_o$; counting the values of $N_p$ and $N_{p+1}$ of the number of particles of charges pe and (P+1)e fixed by the selector and calculating by the formula $$N_o = N_p \exp\left(\frac{n}{2}\left[p^2 - 2p\left(p + \frac{1}{2} - \frac{1}{n}\ln\frac{N_p}{N_{p+1}}\right)\right]\right)$$

the number $N_o$ representing the number of neutral particles supplied to the counter and comparing $N'_o$ with $N_p$. An apparatus using above process to separately pick-up the charged particles with a view to count the numbers $N_p$ and $N_{p+1}$ contains a particle counter in which particles of the same grain size are produced comprising a cylindrical case containing an annular cylindrical bipolar charge space and a mobility selector linked with the charge space and are superimposed manner within the cylindrical case.

5 Claims, 5 Drawing Sheets

PROCESS AND APPARATUS FOR CALIBRATING A PARTICLE COUNTER

The present invention relates to methods and apparatuses making it possible to calibrate an aerosol particle counter, i.e. an apparatus able to determine the concentration (number of particles per volume unit) of a given aerosol and if possible the grain size spectrum of the said particles.

In general terms, various methods are already known and used in industry for determining the size and/or concentration of particles suspended in the atmosphere, said methods being performed in the said counters.

One method for calibrating these counters is based on the examination of a characteristic quantity of particles of an aerosol referred to as its electrical mobility. This quantity, which defines the varying aptitude of such a particle to undergo a deflection under the effect of an electrostatic field can be expressed by the following equation:

$$\vec{W} = Z\vec{E}$$

In said vector equation W is the drift velocity acquired by the particle under the influence of the electrical field $\vec{E}$ to which it is exposed. The proportionality coefficient Z between the two preceding quantities is the electrical mobility in question. This electrical mobility, which is on the one hand proportional to the electrical charge of the particle and on the other hand is inversely proportional to its grain size, which is also in accordance with intuition.

There are also equipments called "analysers" or "selectors" or differential mobility making it possible with the aid of electrostatic means to separate, as a function of their own electrical mobility, the different particles belonging to a given aerosol flux. At present the concentration or grain size calibration methods of aerosol particle counters based on the use of such an electrical mobility selector are the most widely used. Before describing the invention in detail, certain information will be given thereon.

With regards to the grain size or dimensional calibration of the particle counters of an aerosol, the methods used in a completely satisfactory manner up to now consist either of producing the aerosol from calibrated particles, or preparing the aerosol from a solution of a salt in water. In the first case use is e.g. made of latex polystyrene microspheres, whose known diameter is between 0.1 and 10 micrometers and then using a pneumatic machine a liquid suspension of said calibrated particles is atomized. After atomization and drying, the particle flux is subdivided into several families, namely:
a) dry residues resulting from the evaporation of droplets not carrying latex spheres (these are impurities);
b) dry residues resulting from the evaporation of droplets carrying a single microsphere (singlets);
c) residues resulting from the evaporation of droplets carrying two microspheres (doublets), etc.

Thus, there is a discontinuous size particle spectrum constituted by impurities, singlets, doublets, triplets, etc. In order to obtain a standard flux of given grain size, it is necessary to select a particular family from those mentioned hereinbefore, which can be carried out without difficulty with the aid of an electrical mobility selector.

In the second case if the starting aerosol is not constituted by a suspension of precalibrated particles, it can e.g. be an aerosol obtained by the atomization of a solution of a salt in water, a dry residue is obtained after drying, which is constituted by polydispersed particles, i.e. whose grain sizes can vary in a random and continuous manner within a given range. In this case it is merely necessary to pass this aerosol into a differential mobility selector to obtain at its outlet quasimonodispersed particles, i.e. all having the same grain size and directly usuable for the calibration of a counter.

The invention more particularly relates to the concentration calibration, i.e. the number of particles per volume unit. The problem is more difficult and one of the presently used known apparatuses for carrying out said calibration is described by Jugal K. Agarwal and Michel Pourprix in the article entitled "A continuous flow CNC capable of counting single particles", published in the proceedings of the 9th International Conference on Atmospheric Aerosols, Condensation and Ice Nuclei, Galway, Ireland, 1977. The apparatus and process described in this article are based on the two following essential characteristics.

Firstly, the aerosol on which working takes place is a monodispersed aerosol, all of whose particles carry a single electrical charge. The Expert knows how to obtain such a particle population by the methods described hereinbefore (e.g. calibrated latex spheres from an electrically mobility selector).

In addition, the sought concentration is measured with the aid of the electrical current induced by the charged particle flux during the passage of the particles into an electrometer arranged parallel to the counter to be tested. The current i measured by this electrometer is expressed by the equation $i = QNe$, in which Q is the aerosol flow rate in $cm^3/s$, N is the particle concentration per $cm^3$ and e the elementary electrical charge of $1.6 \cdot 10^{-19}$ Coulomb.

Knowing i and Q from the same it is easily possible, at least in theory, to deduce the value N of the concentration of particles per $cm^3$ in the aerosol flow. This known process suffers from a single disadvantage. Thus, it is necessary to assume that the distribution of the aerosol flux between the counter to be calibrated and the measuring electrometer are known.

Moreover, the development of certain new and in particular electronic methods involving the production of large air volumes with a very high purity level, i.e. a low particle concentration (white rooms), make it necessary to be able to estimate concentrations in the atmosphere of typically 10 to 100 particles per cubic foot, i.e. 10 to 100 particles in 28,000 $cm^3$. However, the best known calibration methods and in particular those described hereinbefore do not make it possible to measure concentrations below 200 particles/$cm^3$, i.e. approximately $5.6 \cdot 10^{-6}$ particles/cubic foot. Thus, a very important problem is not solved at present, because the best known calibration methods are limited to concentrations approximately $10^4$ times higher than those which it would be necessary to reach for carrying out calibrations in a measuring range compatible with the standards applicable under ultra-clean conditions.

The present invention specifically relates to a process for calibrating aerosol particle counters making it possible by using means which are simple to put into effect to obtain a quasi-absolute measurement of the concentration of particles of an aerosol and even concentrations such as those of ultra-clean atmospheres.

The process for calibrating a particle counter according to the invention is characterized by the following stages:

- an aerosol of particles of the same grain size (monodispersed) is formed in a vector gas flow;
- said aerosol is exposed to the action of a bipolar charger, e.g. constituted by an ionizing radioactive source able to develop, in the vector gas of the aerosol, ions of two signs which electrically charge the particles and bring them to a stationary charge state in which the distribution of the number of charges fixed to each particle follows a Gaussian law (Gunn or Boltzmann);
- the thus charged aerosol is passed into a mobility selector which, on the one hand, fixes the charged particles to the electrodes classifying them as a function of the number p of their elementary electrical charges e and, on the other hand, allowing to escape the electrically neutral particles;
- these neutral particles are collected and passed into the particle counter to be calibrated, which displays a value $N'_o$;
- the numbers $N_p$ and $N_{(p+1)}$ of the particles of charges pe and (p+1)e fixed by the selector are counted and from the same is deduced the number $N_o$ of neutral particles really fed into the counter by the formula $$N_o = N_p \exp\left\{\frac{\eta}{2}\left[p^2 - 2p\left(p + \frac{1}{2} - \frac{1}{\eta}\ln\frac{N_p}{N_{p+1}}\right)\right]\right\}$$

in which $$\eta = \frac{2e^2}{dKT}$$

in which d is the diameter of the particles, K the Boltzmann constant, T the absolute temperature in Kelvins and ln the natural logarithm;

$N'_o$ and $N_o$ are compared.

As can be seen, the above process is essentially based on the two following physical phenomena.

Firstly, the charging laws of aerosols in a bipolar ionized medium lead to a stationary electrical state, in which the distribution of the number of charges fixed to each particle follows a Gaussian law (Boltzmann or Gunn law) in the form:

$$\frac{N_p}{Z} = \sqrt{\frac{e^2}{\pi dKT}} \exp\left[\frac{-(p-\bar{p})^2 e^2}{dKT}\right]$$

in which
- e is the elementary electrical charge ($4.8 \cdot 10^{-10}$ ues cgs)
- d the diameter of the particles (cm)
- K the Boltzmann constant ($1.38 \cdot 10^{-16}$ erg/°)
- T is the absolute temperature (°K)
- p is the number of electrical charges carried by the particles
- $\bar{p}$ is the mean charge of the aerosol (if $\bar{p}=0$, Boltzmann law, if $\bar{p} \neq 0$, Gunn law)
- $N_p$ is the number of particles carrying p charges per volume unit (cm$^{-3}$)
- Z is the total number of particles (cm$^{-3}$).

Finally, the very particular form of this Gaussian charge distribution law makes it possible to link the numbers No of neutral particles of a thus charged aerosol and the numbers $N_p$ and $N_{p+1}$ of particles of said aerosol having p elementary charges and p+1 elementary charges, in accordance with the formula:

$$N_o = N_p \exp\left\{\frac{\eta}{2}\left[p^2 - 2p\left(p + \frac{1}{2} - \frac{1}{\eta}\ln\frac{N_p}{N_{p+1}}\right)\right]\right\}$$

It is therefore easy by using a particle electrical mobility selector, to separately detect the charged particles with a view to selecting the numbers $N_p$ and $N_{p+1}$, to deduce therefrom in accordance with the above formula the number of neutral particles $N_o$ contained in the said aerosol and to feed them to a counter to be tested, in order to finally compare this calculated number with the actual counter reading. This arrangement makes it possible to remove the uncertainty concerning the distribution of the particles between the counter to be tested and the standard sensor, which is one of the defects of the prior art process. It also makes it possible to utilize very accurate surface deposit coupling methods.

This method has the advantage of being an absolute method. It is essentially dependent on the accuracy with which it is possible to count $N_p$ and $N_{p+1}$, ±5% being the typical uncertainty range. Moreover, it makes it possible to calibrate counters at ultra-low particle concentrations, such as are nowadays encountered e.g. in white rooms. Compared with the prior art methods, the invention makes it possible to reduce by a factor of approximately $10^4$ the particle concentrations necessary for carrying out the calibration of counters, which are thus calibrated in their white room use ranges.

Obviously, the mobility selector used in the process according to the invention can, at least in theory, be of a random nature and can be one of the selectors most widely used hitherto having a planar longitudinal geometry or an axial cylindrical geometry.

However, the Applicant has found that a new type of mobility selector was able to permit a simpler and more reliable performance of the process according to the invention. This mobility selector is an electrostatic sensor comprising two spaced, parallel, coaxial conductor disks between which is established an electrical field by raising them to different potentials, the space between the two disks communicating over its entire periphery with the atmosphere to be examined, a central suction system being provided in the said space so as to bring about a circulation there, from the periphery of the disks, of part of the said atmosphere in the form of a stable, centripetal, laminar flow.

In its simplest form shown in FIG. 1, said electrostatic sensor used as a mobility selector is constructed in the following way. The sensor essentially comprises a flattened, circular, cylindrical case 2, provided along its central axis with an inlet 4 for the injection flow $Q_o$ of entraining gas under the action of a pump 6. Along the same axis, but in the upper part is provided a discharge pipe 8 for the atmosphere sucked in under the action of the suction pump 10. In the upper part of the case 2 is provided an annular slot 12 for the penetration of the atmosphere to be examined under the angle of its aerosol particle content. The sampling flow rate Q1 of the gas to be examined in order to make it flow in the case 1 results from the difference between the gas suction flow rate Q2 under the action of the pump 10 and the injection flow rate $Q_o$ at the inlet and under the action of the pump 6.

Within the case 2 is provided a solid, thick disk 14, which may or may not conduct electricity, on whose upper surface rests one of the two coaxial conductor disks 16 which, together with the upper part 18 of the case 2, form the two coaxial, conductor disks characteristic of the invention. The upper disk 18 is connected to earth or ground, whereas the lower disk 16 is brought to a high positive or negative voltage with respect to the said earth or ground. The entraining gas moved by the pump 6 and injected into the pipe 4 penetrates the case 2 by the lower part and is distributed therein in accordance with a symmetry of revolution symbolized by the arrows F and traverses an annular filter 20, which completely purifies the same whilst eliminating all suspended particles which it can contain and also regularizes the flow. Once this gas has been filtered it passes round the upper part of the thick disk 14 and gives the atmosphere flow Q1 to be examined a stable, centripetal, laminar flow in the space between the two coaxial, conductor disks 16 and 18. The said gas is then subject to suction action in the centre of the apparatus by the pipe 8 under the effect of the pump 10. After a certain operating time necessary for the electrostatic trapping on the disks 16 and 18 of the aerosol particles contained in the atmosphere flow sampled through the opening 12, it is possible to open the apparatus and observe the disk 16, which has the appearance represented in FIG. 2 and where it is possible to see the particles having a given sign, if they are all of the same grain size, deposited in concentric, annular zones corresponding to their different electrical mobilities, i.e. to their different electrical charges, 1,2, . . . p, p+1.

Therefore the number of particles of the different consecutive annular zones is related to the values $N_1$, $N_2 \ldots N_p$, $N_{p+1}$ referred to hereinbefore and which the Expert knows how to count using a surface deposit analyser and per se known data processing.

This type of electrical mobility particle selector makes it possible through its circular symmetry and its stable, centripetal, laminar gas flow to bring about a total collection of the charged particles (whilst regulating the potential difference between the disks 16 and 18 and the flow rate $Q_2$ for this purpose), as well as an easy counting thereof by annular zones with the aid of known data processing means.

Thus, the counting of particles carrying p and p+1 charges deposited on two consecutive, concentric, annular zones permits the precise calculation of the number $N_o$ of neutral particles contained in the examined aerosol. In practical terms, usually this calculation is carried out on the basis of numbers $N_1$ and $N_2$ of particles carrying one and two elementary charges, i.e. two first annular zones.

If in theory the calculation of $N_o$ from $N_p$ and $N_{p+1}$ can be carried out according to the previously given formula, it is more usual to utilize the following formula, which is derived from the first formula and which gives the value of $N_o$ as a function of the numbers of particles $C_1$ and $C_2$ respectively carrying one and two elementary charges, such that they can be counted on the deposit surface and as deposited throughout the time $\Delta t$ of the said deposit. This formula is written in the following way $$N_o = \frac{C_1}{Q_o \Delta t} \exp\left[\frac{-e^2}{dKT}\left(2 - \frac{dKT}{e^2}\ln\frac{C_1}{C_2}\right)\right]$$

with $N_o$ being the concentration of standard neutral particles (particle/cm$^3$), $Q_o$ is the extraction flow rate of the electrostatic sensor (cm$^3$/s), $\Delta t$ is the time during which the deposit takes place(s), whilst $C_1$ and $C_2$ represent the number of particles carrying one and two charges, counted on the deposit surface and directly related to the previously defined concentrations $N_1$ and $N_2$.

The Applicant has found that it was possible when the calibration process of a particle counter according to the invention was performed with the aid of an electrical mobility selector having a circular symmetry and a centripetal flow, to obtain a particularly simple and compact calibration apparatus, whose integrated form makes it particularly easy to use.

This apparatus for performing the calibration process of a particle counter, in which the particles of the same grain size are produced by selective electrostatic filtration, in a first mobility selector, of a primary aerosol having several discrete grain sizes is characterized in that it comprises, in the same cylindrical case and positioned one below the other, an annular cylindrical bipolar charging space e.g. having an ionizing source and receiving an aerosol of monodispersed particles, and a mobility selector communicating with the charging space and dispersing on its electrodes and as a function of their charges, all the charged particles which it receives, the suction flow rate of said mobility selector only containing the neutral particles to be counted.

Preferably, the apparatus also has an electrical mobility preselector with a circular symmetry. As a result of this preselector, at the inlet it can receive the primary aerosol having several different grain sizes. Preferably, the apparatus also has a primary aerosol injection chamber linked with the bipolar charging space either directly, or via the electrical mobility preselector.

In its preferred embodiment, the calibration apparatus according to the invention combines in the same cylindrical case and in four superimposed stages the injection functions of the first and second mobility selectors and the bipolar charging means. The two mobility selector stages are separated by an ionizing chamber having an e.g. alpha radioactive source, which brings about the bipolar charging of the aerosol particles, which is a characteristic of one of the essential stages of the calibration process according to the invention.

The invention is described in greater detail hereinafter relative to non-limitative embodiments and the attached drawings, wherein show:

FIG. 1 the diagram of a charged particle electrical mobility selector with circular symmetry and a centripetal laminar flow.

Figure 2:
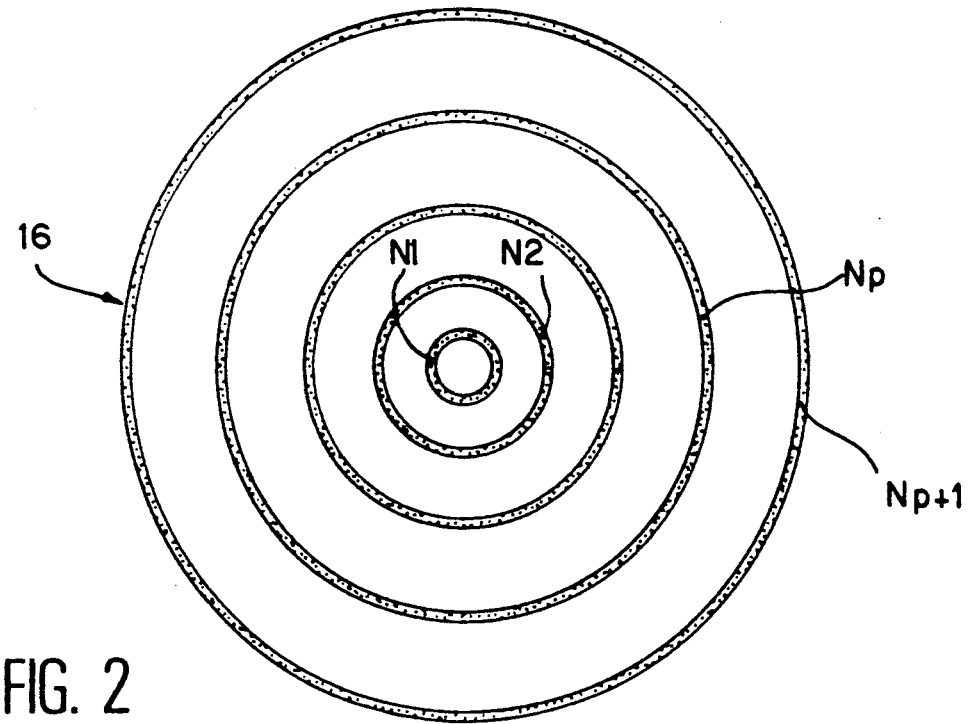

FIG. 2 in plan view the deposits, in the form of successive annular zones, of particles dispersed as a function of their charge on the collection plate of the apparatus of FIG. 1.

FIGS. 3a to 3d the distribution of the electrical charges of the particles of an aerosol exposed to the action of a bipolar charger in the case of a so-called Boltzmann symmetrical distribution.

Figure 4:
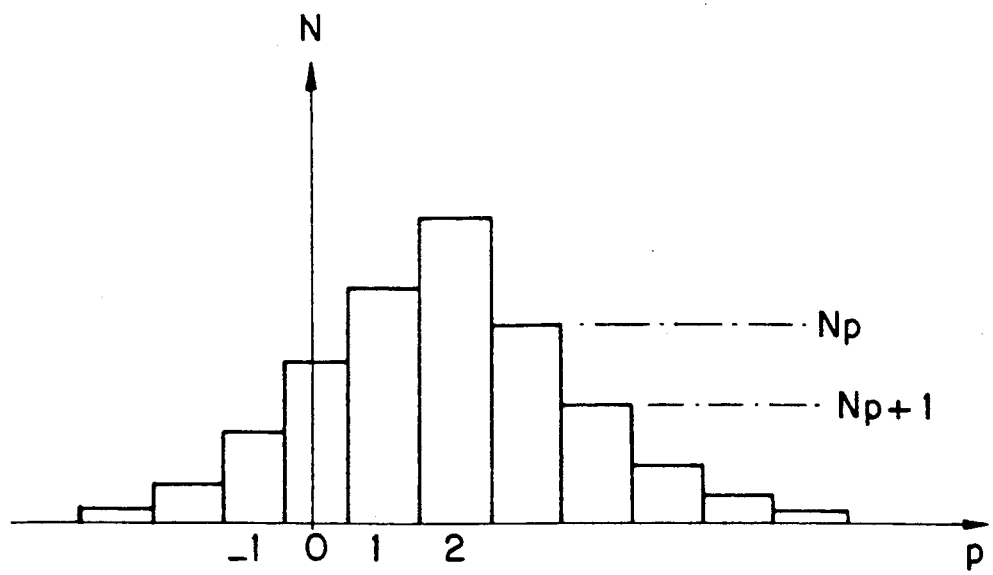

FIG. 4 the same charges of a particle flux in the case of an equilibrium differing from that of Boltzmann and known as the Gunn equilibrium.

Figure 5:
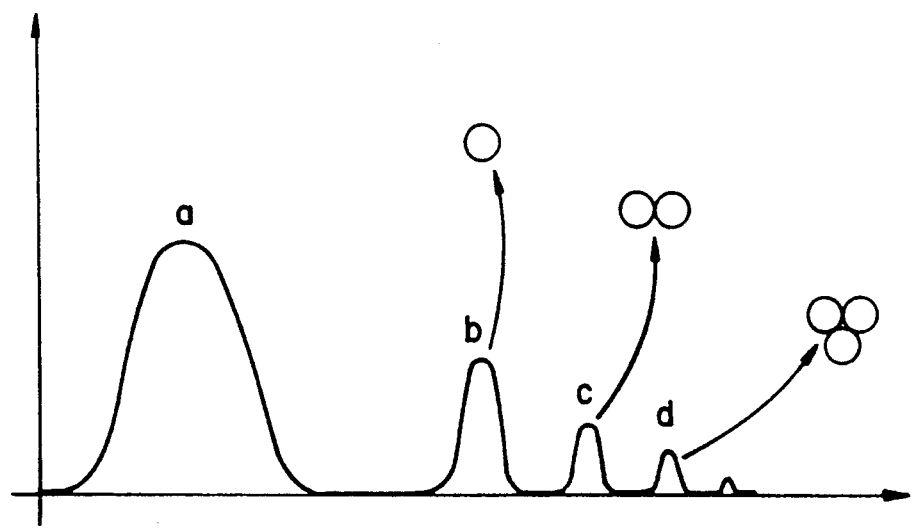

FIG. 5 the grain size spectrum of the particles obtained during the preparation of an aerosol by spraying a solution of precalibrated latex polystyrene spheres or balls.

Figure 6:
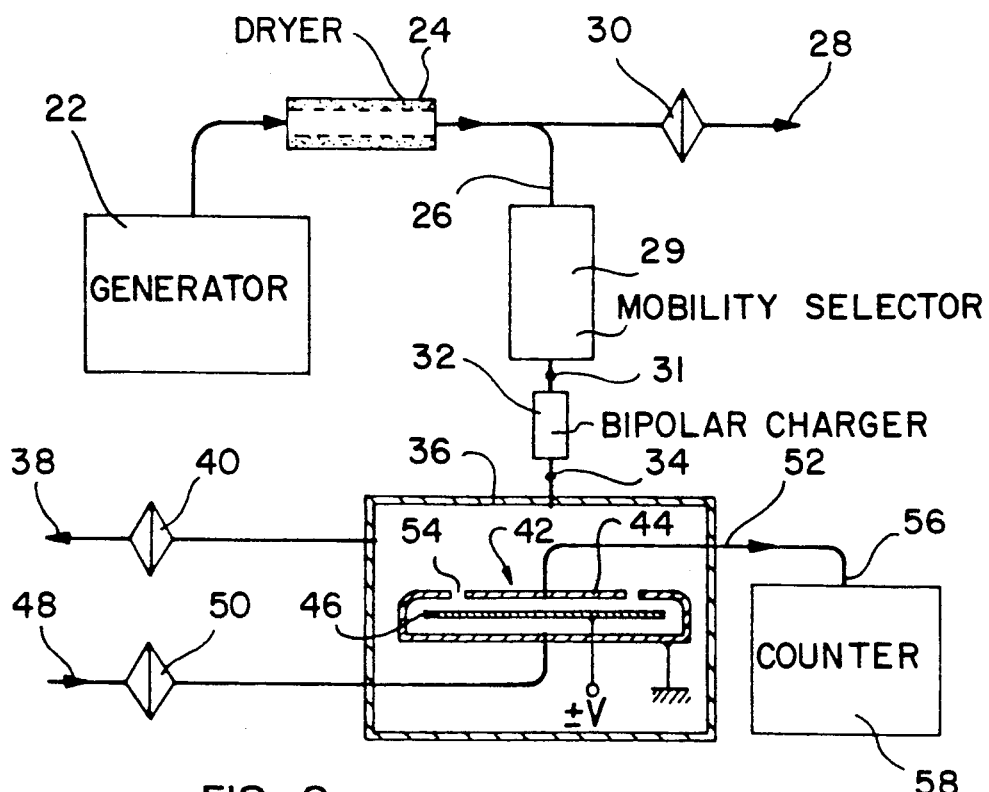

FIG. 6 the diagram of an installation for performing the calibration process according to the invention in the general case.

Figure 7:
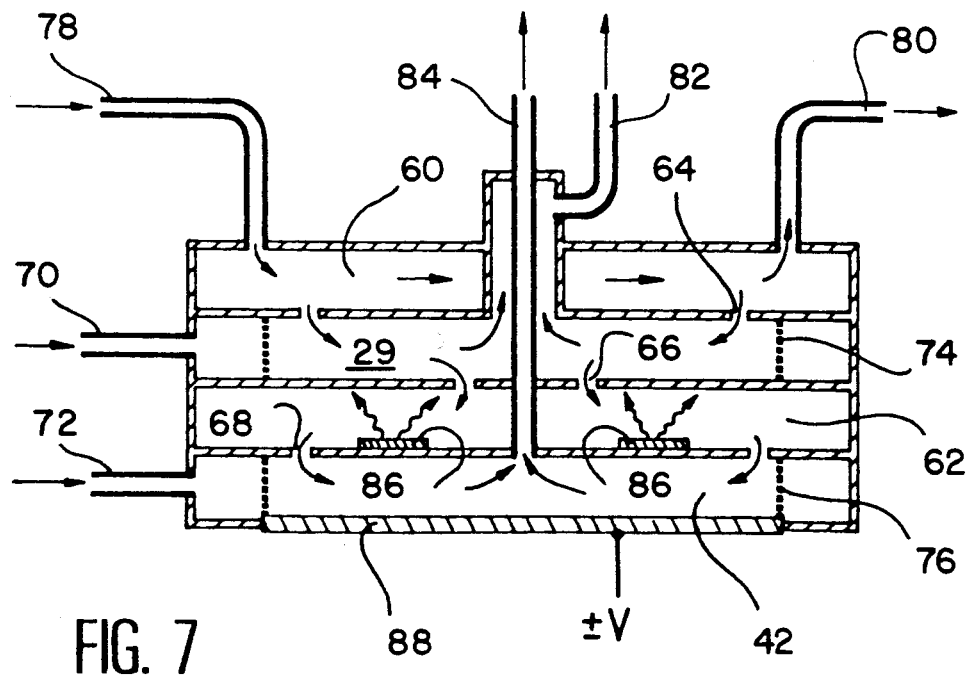

FIG. 7 the diagram of a calibrating apparatus for a particle counter according to the invention.

Figure 8:
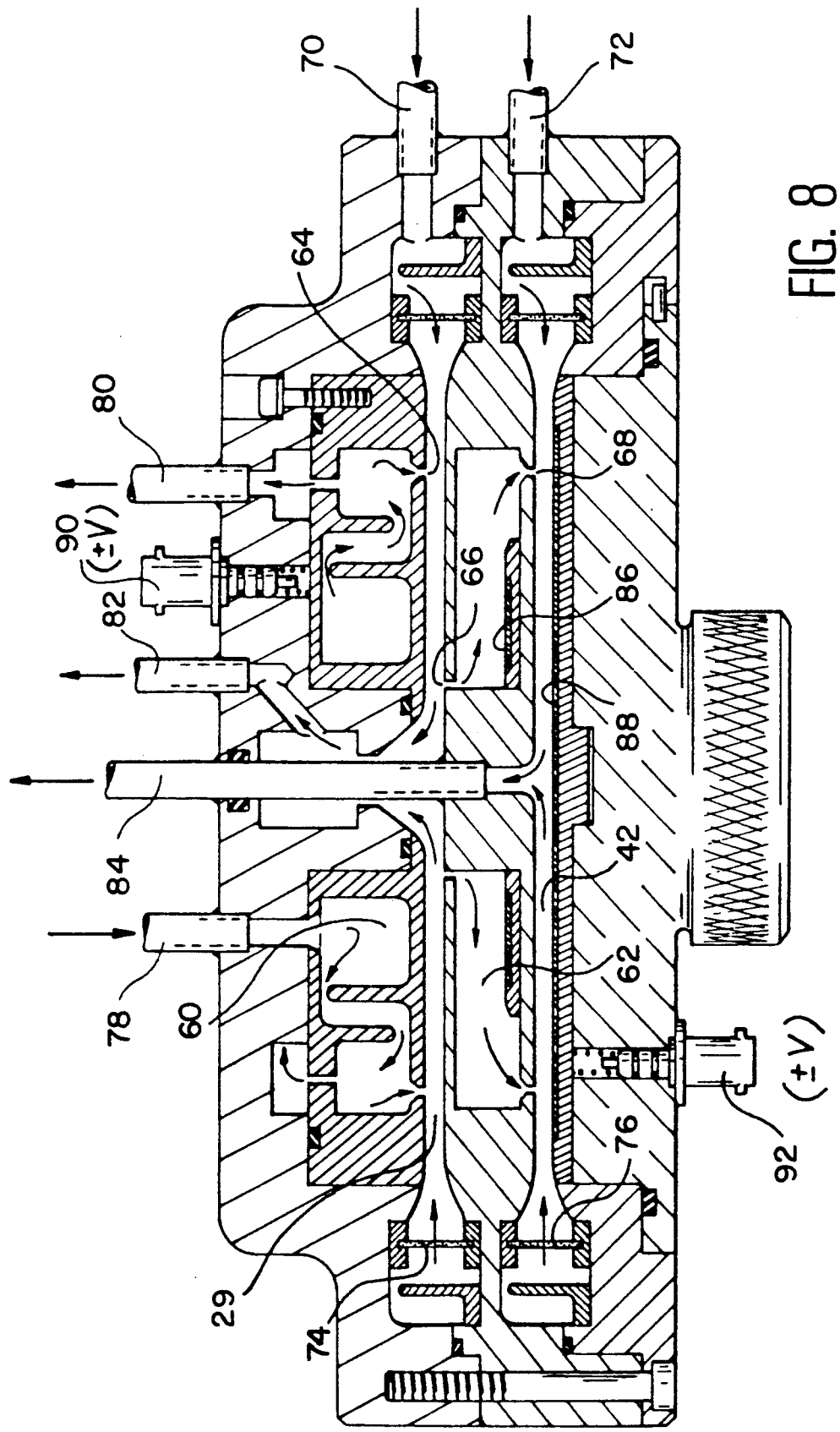

FIG. 8 in greater detail the industrial embodiment of the diagram of FIG. 7.

FIGS. 1 and 2, which have already been described, illustrate a particular construction of the electrical mobility selector more particularly applicable to the case of the process of the present invention.

Figure 3A:
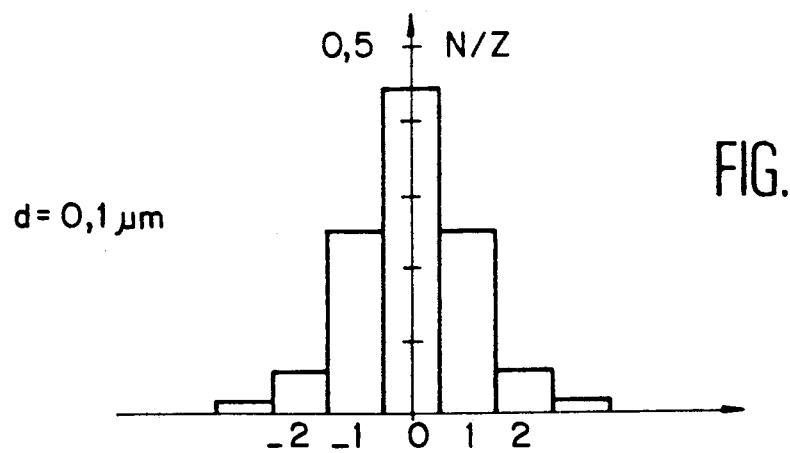
Figure 3B:
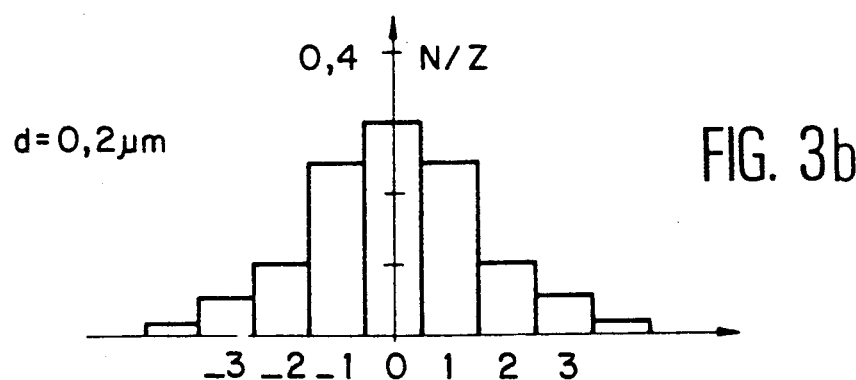
Figure 3C:
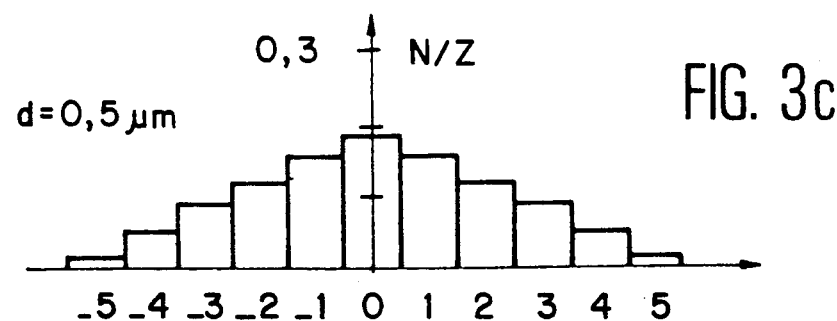
Figure 3D:
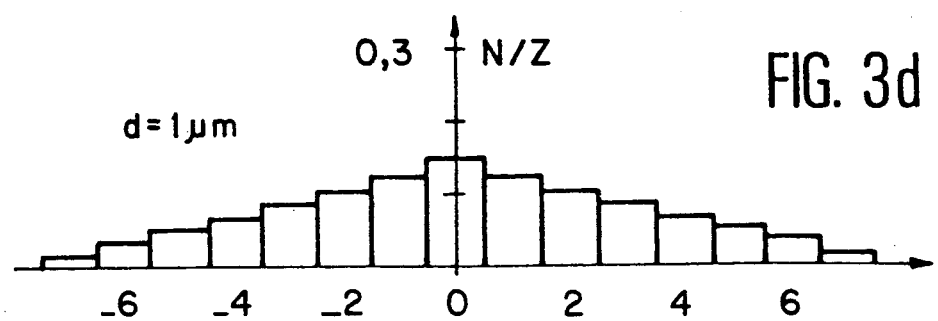

FIGS. 3*a* to 3*d* make it possible to understand the effect of the bipolar charging phase of the particles of an aerosol with the aid of ions of both signs produced in the vector gas of said same aerosol. On the abscissa appears the number of charges by particles and on the ordinate in reduced coordinates the number of particles having a given electrical charge relative to the total number of particles. FIG. 3*a* relates to particles with a diameter of 0.1 micrometer, FIG. 3*b* to particles of 0.2 micrometer, FIG. 3*c* to particles of 0.5 micrometer and FIG. 3*d* to particles of 1 micrometer. The hypothesis illustrated in FIGS. 3*a* to 3*d* is that of a Boltzmann distribution in which the aerosol is overall neutral and in which the charged particles of one sign are in equal numbers compared with those charged with the opposite sign. It is possible to see in the manner known to the Expert that the larger the diameter of the particles, the less neutral particles there are and the more particles there are carrying charges which are a multiple of the elementary charge e.

The interest of the Boltzmann distribution is that, as has been revealed by the Applicant, the knowledge of the number of particles carrying p charges and the number of particles carrying p+1 charges, or in other words the knowledge of the two points of the preceding "curve" makes it possible to determine the number of particles $N_o$ which are not charged. In the particular case of the presently described Boltzmann configuration, even in theory it is sufficient to e.g. know the number $N_1$ of particles having an elementary charge to determine the number of neutral particles $N_o$.

In the general case of a bipolar charging, as described hereinbefore, the equilibrium obtained by the different charges on the particles is an equilibrium in accordance with Gunn's law in the manner shown in FIG. 4 and which differs from that referred to hereinbefore by the fact that the charge distribution "curve" is no longer symmetrical around the band corresponding to the neutral particles $N_o$. In both cases the knowledge of two random consecutive values of the number of particles $N_p$ and $N_{p+1}$ makes it possible to determine the number of neutral particles $N_o$, which is the essential condition making it possible to perform the process according to the invention. Thus, it is the bipolar charging phase of the gas vector of the particles of a given aerosol which makes it possible, by applying the preceding characteristics of the charge spectra, to determine the exact number $N_o$ of neutral particles contained in a given aerosol flux and therefore perform the process of the invention.

On referring to FIG. 5 an explanation will be given of the physical phenomena which occur when, for calibrating in grain size a particle counter, an aerosol of standard grain size is produced from precalibrated latex polystyrene microspheres. For this purpose, the most widely used process consists of suspending in a gas, generally air, monodispersed aerosols, i.e. all of whose particles have the same grain size.

For this purpose, use is made of latex polystyrene microspheres marketed by several manufacturers and whose particle diameter is generally between 0.1 and 10 micrometers with an extremely small standard deviation of approximately 1%. Firstly a liquid suspension of such calibrated particles is formed, generally in ultrapure water. This liquid is then atomized by pneumatic means suspending the droplets in the vector gas. The aforementioned preparation method obviously leads to an aerosol, whose particles have variable dimensions, because they can have 0,1,2 or p latex microspheres. After drying these droplets, the gas flow obtained has in suspension several families of particles, namely those whose concentration is shown in FIG. 5 as a function of their diameter.

The different concentration peaks shown in FIG. 5 correspond to the following cases:

Peak a corresponds to dry residues resulting from the evaporation of droplets, whereof all that is left are certain impurities, but no latex microspheres.

Peak b corresponds to dry residues resulting from the evaporation of droplets carrying a single microsphere (these droplets can be called singlets).

Peak c corresponds to dry residues resulting from the evaporation of droplets carrying two microspheres (which can be called doublets).

Peak d corresponds to triplets, etc.

The different families of particles also carry, as a result of the friction which has occurred during atomization, a random number of electrical charges, but which is obviously equal to a multiple of the elementary electrical charge e.

In accordance with a known procedure, it is merely necessary to pass such a particle flux into a mobility selector in order to obtain at its outlet and obviously as a function of the chosen setting, a flux of particles all having the same grain size (monodispersed) and having a single electrical charge. In other words, this passage into an electrical mobility selector makes it possible to select the group b of singlets of FIG. 5, which all have the elementary electrical charge e.

FIG. 6 shows the diagram of an installation making it possible to perform the process of calibrating a particle counter according to the invention. It shows a latex microsphere aerosol generator 22 functioning in the manner described relative to FIG. 5. At the outlet from said aerosol generator 22, the particle flux passes through a dryer 24 and the part 26 of the aerosol flux which has not been discharged to the outside at 28 through a filter 30, penetrates a first electrical mobility differential analyser or electrical mobility selector 29. The latter is regulated in such a way as to only allow to pass through its outlet 31 monodispersed particles, e.g. singlets, all having the same unitary electrical charge e. This aerosol flux is then passed to a bipolar charger 32, which is a space in which an e.g. alpha ionizing radioactive source ionizes the vector gas of the aerosol causing the appearance therein of gas ions of both signs. This ionized vector gas in turn charges the particles of the aerosol which are then in the stationary electrical equilibrium of FIGS. 3 or 4. The thus charged aerosol flux is then injected into a second differential mobility selector in the following way.

At the outlet 34 from the bipolar charger 32, the gas flux is injected into a sealed enclosure 36 having a pipe 38 for dicharging any gas excess through the filter 40. In said enclosure 36, which is therefore rapidly entirely filled with the vector gas in the preceding stationary electrical equilibrium, is located in the second mobility selector 42 and which, as indicated in FIG. 6, can be an electrical mobility selector with circular symmetry and a centripetal, gas flow. This mobility selector 42 has two electrodes respectively connected for the external electrode 44 to earth and for the internal electrode 46 to a high potential of $\pm V$ typically of several thousand volts for particles having a diameter of approximately 1 micrometer. The mobility selector 42 is traversed by an entraining gas entering the same through the inlet 48 across the filter 50 and passes out of the same at 52. According to the invention, the selector 42 has a suction slot 54 by which the aforementioned entraining gas flux sucks the vector gas from the aerosol and makes it pass into the vicinity of the electrode 46. As the latter is charged to a high fixed negative or positive voltage, in the manner shown in FIG. 2, the different charged particles of the aerosol vector gas are distributed into concentric annular zones, each of which corresponding to particles having an integral number of elementary electrical charges.

In principle, the mobility selector 42 is regulated so as to fix all the electrical particles of both signs on the two electrodes 44 and 46 and only allows the passing out at 52 of the uncharged neutral particles in concentration $N_o$. According to the invention, said neutral particle flux is supplied to the intake 56 of a counter 58 to be calibrated and it is then merely necessary to compare the number $N_o$ calculated on the basis of the aforementioned formula linking $N_p$, $N_{(p+1)}$ and $N_o$ with the reading of the counter 58 to be able to carry out an absolute calibration of said particle counter.

Obviously, for the precise calculation of the number $N_o$ of neutral particles supplied to the particle counter 58 to be tested, as a function of the case, one or other of the two formulas given hereinbefore is used, said formulas being equivalent and are directly derived from one another.

FIG. 7 shows a particularly interesting embodiment of the apparatus of FIG. 6. The Applicant has found that if the two electrical mobility selectors 29 and 42 of FIG. 6 were produced in the form of circular selectors with a radial flow, it was possible to concentrate the essence of the apparatus in a single cylindrical case. Such a case, shown in FIG. 7, has in juxtaposed superimposed manner the first mobility selector 29, the second mobility selector 42, as well as an injection chamber 60 and a bipolar charging chamber 62. These different components communicate pairwise with one another, namely the injection chamber 60 with the first mobility selector 29 via the annular slot 64, the first mobility selector 29 and the bipolar charging chamber 62 via the annular slot 66 and the charging chamber 62 and the second electrical mobility selector 42 via the annular slot 68.

The entraining gas inlets of the two mobility selectors 29 and 42 are respectively located at 70 and 72 across entraining filters 74 and 76. The primary aerosols from the generator 22 of FIG. 6 are introduced into the apparatus at 78 and enter the injection chamber 60. The unused part of said primary aerosols is discharged to the outside by the duct 80. The first mobility selector 29 is connected to a suction tube 82, which discharges to the outside the gas flow which has entered said same selector at 70, whereas the suction tube of the second mobility selector 42 is located in accordance with the axis of the apparatus at 84 and, according to the invention, only the neutral particles of the aerosols extracted from the chamber 62 pass out through the said tube.

The annular outlet slot 66 of the first mobility selector 29 is at a radial distance from the axis of the apparatus chosen as a function of the grain size and the electrical characteristics of that part of the aerosol which is to be sucked by the slot 66 into the bipolar charging space 62. In the manner diagrammatically shown in FIG. 7, said space 62 has a radioactive ionizing source 86 for charging with ions of both signs in accordance with the Boltzmann or Gunn law the vector gas of the aerosol part which has entered via slot 66 into the charging space 62.

The feed slot 68 of the second electrical mobility selector 42 is located on the periphery of the latter, so as to permit a flow of the aerosol-charged gas phase along the collecting electrode 88 for the aerosol-charged particles. According to the invention, the electrical voltage $\pm V$ to which is raised said collecting electrode 88 is chosen, as is the suction flow into the pipe 84 on leaving the selector 42, in such a way as to permit the collection on the electrode disk 88 of all the electrical charges which have entered the selector 42 and so as to only allow the suction through the outlet 84 of the neutral particles, which are then supplied to the counter 58 to be tested and which is not shown in FIG. 7.

With reference to FIG. 8, an industrial embodiment of the integrated structure of FIG. 7 will be described. FIG. 8 essentially shows a compact cylindrical block into which are integrated in juxtaposed manner the injection chamber 60, the first mobility selector 29, the bipolar charging chamber 62 and the second electrical mobility selector 42. It is also possible to see in FIG. 8 the tube 28 for introducing primary aerosols, the inlets 70 and 72 for the entrainment gas flows from the mobility selectors 29 and 42, as well as the suction outlet 62 of the first mobility selector 29 and the outlet reserved for the calibrated neutral particles 84. The radioactive source 86 is located at the bottom of the bipolar charging enclosure 62 and the two high voltage supplies 90 and 92 are respectively provided for the first mobility selector 29 and the second mobility selector 42. There are also annular slots 64, 66 and 68 enabling the useful part of the gas flow to pass from one stage to the next. The structure of FIG. 8 is remarkable as a result of its compactness and ease of use compared with that shown in FIG. 6 (references 26 to 32) associating the elementary functions necessary for leading to the same results.

I claim:

1. A method for calibrating a particle counter comprising the following steps;

forming a vector gas flow by an aerosol of particles of the same grain size;

developing ions in the vector gas with both sign by a bipolar charger, certain particles being electrically charged to a stationary charge state in which the distribution of the number of charges fixed to each particle follows a Gaussian law (Gunn or Boltzmann);

passing the charge aerosol into a mobility selector to attract the charged particles to electrodes therein and classify them as a function of the numbers p of their elementary electrical charges e and allowing said electrically neutral particles to escape;

collecting said neutral particles and passing said neutral particles into said particle counter to be calibrated, said particles counter displaying a value $N'_o$;

counting the values of $N_p$ and $N_{p+1}$ of said number of particles of charges pe and $(P+1)e$ fixed by said selector and calculating by the formula $$N_o = N_p \exp\left(\frac{n}{2}\left[p^2 - 2p\left(p + \frac{1}{2} - \frac{1}{n}\ln\frac{N_p}{N_{p+1}}\right)\right]\right)$$

the number $N_o$ representing the number of neutral particles supplied to said counter; and comparing $N'_o$ with $N_p$.

2. Apparatus for calibrating a particle counter in which particle of the same grain size are produced comprising;

a cylindrical case;

an annular cylindrical bipolar charge space;

a mobility selector linked with said charge space;

said annular cylindrical bipolar charge space and said mobility selector arranged in a superimposed manner within said cylindrical case;

said mobility selector containing electrodes;

said annular bipolar cylindrical charge space receives an aerosol of monodispersed particles;

said mobility selector disperses on said electrodes all said charged particles which it receives as function their charges;

a suction flow of said mobility selector contains only the neutral particles to be counted.

3. Apparatus according to claim 2 further comprising an electrical mobility preselector with circular symmetry.

4. Apparatus according to claim 2 further comprising a primary aerosol injection chamber linked with said bipolar charge space.

5. Apparatus according to claim 3 further comprising a primary aerosol injection chamber linked with said bipolar charge space.

* * * * *